United States Patent [19]
Hood et al.

[11] Patent Number: 5,746,713
[45] Date of Patent: May 5, 1998

[54] PHACOEMULSIFICATION NEEDLE

[76] Inventors: Larry Hood, 25652 Nottingham Ct., Laguna Hills, Calif. 92653; Tony V. Lemus, 4915 Coolidge Ave., Culver City, Calif. 90230

[21] Appl. No.: 659,630

[22] Filed: Jun. 6, 1996

[51] Int. Cl.⁶ .................................................. A61B 17/00
[52] U.S. Cl. .......................... 604/22; 604/272; 606/107; 606/169
[58] Field of Search .............................. 604/22, 27, 272; 606/107, 169

[56] References Cited

U.S. PATENT DOCUMENTS 5,038,756  8/1991  Kepley ............................ 604/22
5,151,084  9/1992  Khek ............................. 604/22
5,486,162  1/1996  Brumbach ........................ 604/22

*Primary Examiner*—Corrine M. McDermott
*Attorney, Agent, or Firm*—Walter A. Hackler

[57] ABSTRACT

A phacoemulsification needle generally includes a needle for fragmenting eye tissue, a sleeve coaxially disposed about the needle for introducing irrigation fluid into a surgical site, and structure on the needle for inhibiting the formation of bubbles and microbubbles as the irrigation fluid flows along an irrigation pathway formed between the needle and coaxial sleeve. The structure includes preferably three wedge shaped indents, each being equidistantly spaced with respect to each other, about a shoulder of the needle. The needle includes a threaded end for enabling its removable engagement with a suitable phacoemulsification horn, the removable engagement being facilitated by surfaces on the wedge shaped indents.

13 Claims, 1 Drawing Sheet

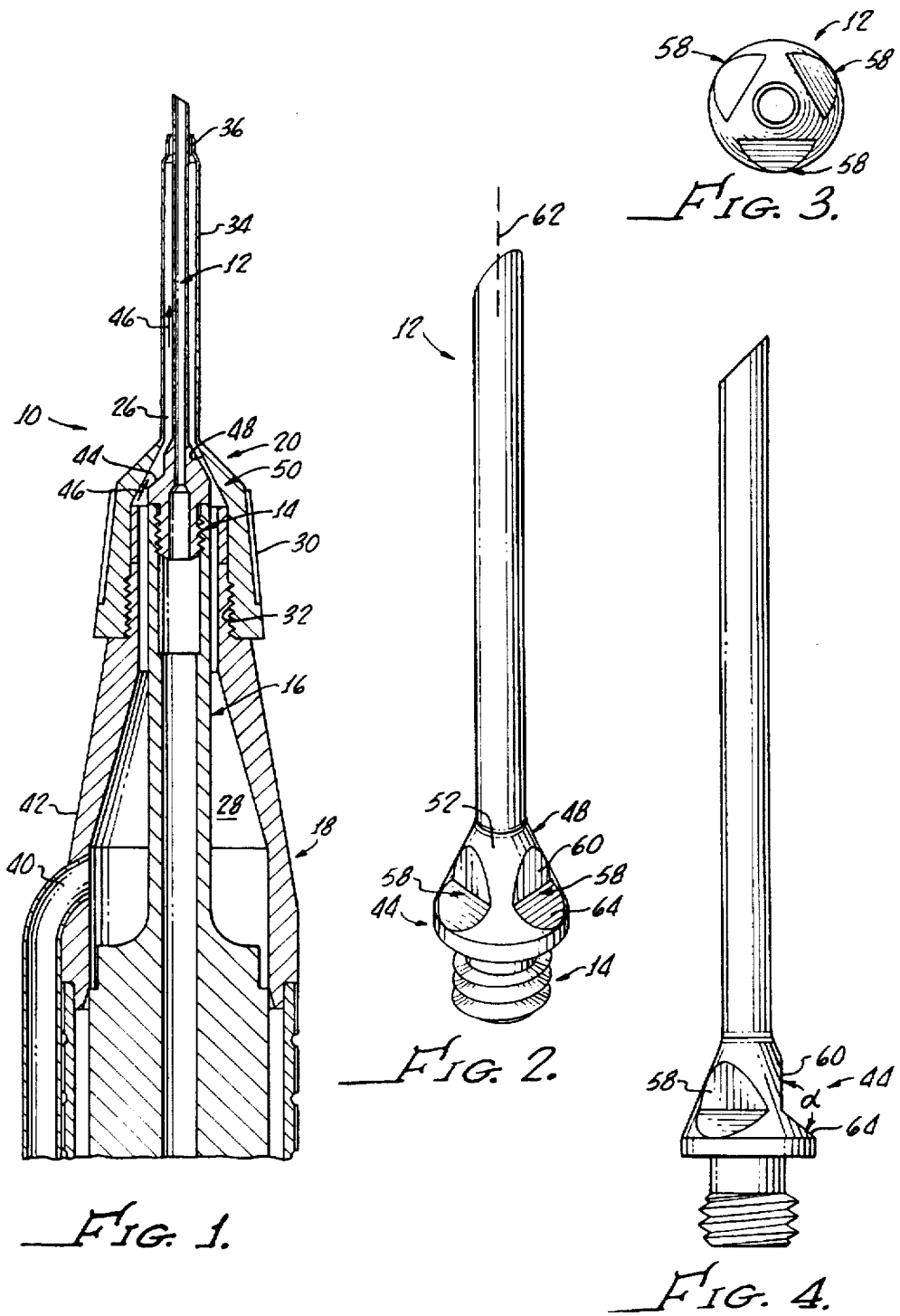

PHACOEMULSIFICATION NEEDLE

The present invention generally relates to surgical instruments and more particularly relates to a phacoemulsification needle for use in ophthalmic surgery.

Phacoemulsification handpieces find common use by ophthalmic surgeons during many in ocular surgical procedures. Phacoemulsification involves the fragmentation of lens tissue and is performed, for example, in cataract surgery.

Because phacoemulsification procedures involve cutting or fragmenting unwanted tissue, the need typically arises to remove tissue and fluids from the eye during the procedure. Furthermore, to prevent damage to the eye, there is also a need to irrigate the surgical site.

Phacoemulsification handpieces that incorporate fragmenting tissue, aspirating and irrigation features have heretofore been developed. These devices enable an optical surgeon to perform several procedures i.e. fragmenting tissue, aspirating fluid and fragmented tissue and irrigating the eye, using a single handpiece and without the need to switch instruments during surgery.

Such compound instruments typically have an cylindrical probe having a cutting tip, or needle, at a distal end thereof. A transducer such as a piezoelectric crystal converts an electrical signal into ultrasonic energy generally in the range of 20 to 100 KHz. The ultrasonic energy generated by the crystal is coupled to a horn and the needle which oscillates and radiates the ultrasonic energy into eye tissue for fragmentation and phacoemulsification thereof.

Additionally, grooves, sleeves or lumen disposed along a length of the needle provide means for introducing irrigation fluids to the surgical site. Many surgeons prefer the use of a sleeve in this regard, as such sleeves may be made to be removable and disposable, thus reducing the risk of cross-contamination.

One significant problem that is experienced by use of prior art phacoemulsification devices, is the cavitation of fluids proximate the tip of the needle and immediately at the surgical site. Cavitation is a well known phenomenon which may be generally described as the of formation of small bubbles in a liquid due to sudden changes in pressure and high frequency vibrations in the liquid.

In ocular surgery, cavitation is caused by the oscillation of the needle tip as well as by changes in pressure of irrigation fluids as they are forced from their respective reservoirs through narrow passages in the needle to be dispensed at the surgical site.

U.S. Pat. No. 5,413,556 describes a prior art phacoemulsification handpiece utilizing an outer shell disposed about the handpiece motor, drive mechanism and horn so as to create an irrigation pathway therebetween. This prior art device allegedly traps cavitation bubbles in a reservoir of significant volume, which is a part of the irrigation pathway near a top of the handpiece, rather than allowing them to flush into the surgical site. Unfortunately, this prior art device does not manage the problems associated with cavitation occurring further down the irrigation pathway, in narrow regions thereof, such as near the site of the needle itself.

Prior art phacoemulsification needles include two standard indents on a proximal end thereof, for the placement of a wrench in order to enable the needle to be threadably fastened to the horn. These indents lie along a narrow irrigation fluid pathway when a sleeve is utilized therefor. It is believed that this standard structure of prior art needles, particularly the two sided placement of indents, is a significant cause of cavitation in the irrigation fluid.

Cavitation results in bubbles that directly obstruct a surgeon's field of view. Furthermore, even microbubbles that are too small to see directly, may seriously distort and obscure view of the surgical site by causing significant changes of the refractive index of the fluids. Consequently, cavitation interferes with the progress of surgery, but may cause increased risk of patient injury. Thus, it often becomes necessary that a surgeon periodically discontinue emulsification and manually remove cavitation bubbles before the surgery can be continued.

Moreover, in many ophthalmic surgical procedures such as, for example, in ocular lens implantation, cataract surgery, and retinal detachment repair, a viscous gel-like composition is utilized to hold the chambers of the eye in order to protect sensitive tissue, in particular the corneal and endothelium, from trauma. Commonly used viscoelastic materials may be classified as either cohesive or adhesive viscoelastic. Generally, cohesive viscoelastic has the property of being cohesive, i.e. molecules thereof tend to stick tightly together rather than to other surfaces. Adherent viscoelastic, on the other hand, tends to adhere to eye surfaces rather than to itself, and thus resists washout during phacosurgery.

Unfortunately, the presence of such viscoelastic materials in the eye increases the potential complications caused by cavitation. Particularly, removal of bubbles becomes a highly complicated task, as the bubbles tend to adhere to viscoelastic materials and resist extraction. As for microbubbles, these are typically so small and numerous that they may not be removed with much success.

Obviously, for the above reasons, it is desirable to have minimal cavitation about the surgical site, particularly when viscoelastic materials are being utilized.

Generally, the present invention provides a phacoemulsification needle that incorporates all the advantages of a compound surgical device while minimizing the occurrence of bubbles and microbubbles during use of the device.

SUMMARY OF THE INVENTION

A phacoemulsification needle apparatus, in accordance with the present invention, generally comprises a needle which provides means for cutting and/or fragmenting eye tissue at a surgical site. The needle includes means, for example a threaded end thereof, for enabling removable engagement of the needle with a suitable phacoemulsification horn. In addition, the apparatus comprises a sleeve that is coaxially disposed about the needle and defines a generally annular chamber between said needle and sleeve. The sleeve provides means for introducing a fluid, for example an irrigation fluid, into the surgical site by way of the generally annular chamber.

Importantly, the present invention also includes structure on said needle which substantially reduces cavitation of the irrigation fluid during its introduction into the surgical site. Particularly, the structure inhibits the formation of bubbles and microbubbles in the annular chamber.

The means for inhibiting the formation of bubbles and microbubbles includes a shoulder on a proximal end of the needle. The shoulder may include a conical surface of revolution and include a plurality of wedge shaped recesses formed therein. The recesses are preferably at least three in number and equidistantly spaced around the conical shoulder.

More particularly, each wedge shaped recess may include a first surface disposed generally parallel to a longitudinal axis of the needle, and a second surface forming an obtuse angle with the first surface. The first surfaces facilitate the

3 attachment and subsequent removal of the needle from the horn by providing surfaces for placement of a wrench.

BRIEF DESCRIPTION OF THE DRAWINGS

The present invention will be more clearly understood when considered in conjunction with the following detailed description and accompanying drawings of which:

FIG. 1 shows a cross-sectional view of a phacoemulsification needle apparatus in accordance with the present invention, the apparatus being connected to a suitable phacoemulsification handpiece horn as used during ocular surgery;

FIG. 2 shows a perspective view of a needle of the phacoemulsification needle apparatus shown in FIG. 1, said needle including structure for inhibiting the formation of bubbles and microbubbles during introduction thereof into a surgical site;

FIG. 3 shows a top view of the needle shown in FIGS. 2; and

FIG. 4 shows a side elevation view of the needle shown in FIG. 2.

DETAILED DESCRIPTION

Turning now to FIG. 1, a phacoemulsification handpiece apparatus 10, in accordance with the present invention, is shown. Generally, the apparatus 10 comprises a needle 12 for cutting and/or fragmenting eye tissue (not shown) at a surgical site by radiating ultrasonic energy into the eye tissue. The needle 10 includes means, such as a threaded end 14, for enabling removable engagement thereof with a horn 16 of a suitable phacoemulsification handpiece 18.

In addition, a sleeve 20, coaxially disposed about the needle 12 and defining a generally annular chamber 26 therebetween, is provided for introducing a fluid 28 into the surgical site. The sleeve 20 may include a proximal end 30 thereof, which is adapted for sealable engagement with the suitable horn 16 by means of threads 32 and an O-ring (not shown) in the conventional manner. An elongated distal end 34 of the sleeve 20 follows the generally tapered contour of the needle 12, and terminates in one or more outlets 36 for dispensing of the fluid 28 at the surgical site. The sleeve 20 may be made of any suitable, inert material of plastic or metal. For preventing cross-contamination, the sleeve 20 and needle 12 are preferably disposable.

The fluid 28 may comprises an irrigation fluid, such as a balanced salt solution, or any other suitable fluid that may be introduced during ocular surgery, and is provided to the chamber 26 from an exterior source (not shown) through, for example, an aperture 40 in a housing 42 of the suitable phacoemulsification handpiece 18.

Importantly, the present invention also includes means, defined by structure 44 on the needle 12, for inhibiting cavitation of the fluid 28 as it moves through the chamber 26, in the direction shown by arrows 46, during introduction of the fluid 28 into the surgical site. This structure 44 is more clearly shown in FIGS. 2, 3 and 4, which illustrate various views of the needle 12.

Particularly, the structure 44 for inhibiting, or substantially reducing the occurrence of bubbles and microbubbles in the annular chamber (not shown in FIGS. 2, 3 and 4) comprises a shoulder 48 on a proximal end 50 of the needle 12. The shoulder 48 preferably has a conical surface of revolution 52 and includes a plurality of recesses 58 therein.

Preferably, three recesses are provided, each recess 58 disposed at about 120 degrees from each adjacent recess 58

4 such that they are equidistantly spaced about the shoulder 48, as shown in FIG. 3.

More particularly, each recess 58 may be wedge shaped and include a first surface 60 disposed generally parallel with a longitudinal axis (indicated by phantom line 62) of the needle 12, and a second surface 64 disposed at an angle (indicated by symbol a in FIG. 4) of at least 90 degrees with respect to the first surface 60. Preferably, the angle α between first and second surfaces 60, 64 is an obtuse angle.

Referring now to all the Figures, the structure 44 hereinabove described substantially reduces fluid turbulence near the point of attachment of the needle 12 with the horn 16, i.e. the needle proximal end 50, which as discussed hereinabove, has been a troublesome area in phacoemulsification handpieces employing prior art needles. As a result, cavitation bubbles are less likely to form in the irrigation fluid 28 as it flows along the restricted irrigation pathway 26. The detrimental effects of cavitation on a surgical procedure are thereby effectively reduced.

Notably, the recesses 58 also provide means for removably engaging the needle 12 to the suitable horn. Specifically, the first surfaces 60 provide locations on which a wrench (not shown), for example a socket wrench, may be positioned for enabling the needle 12 to be threadably engaged to the horn 16.

Although there has been hereinabove described a phacoemulsification needle apparatus in accordance with the present invention for the purpose of illustrating the manner in which the invention may be used to advantage, it will be appreciated that the invention is not limited thereto. Accordingly, any and all modifications, variations, or equivalent arrangements which may occur to those skilled in the art should be considered to be within the scope of the invention as defined in the appended claims.

What is claimed is:

1. A phacoemulsification needle apparatus for ophthalmic surgical procedures, the apparatus comprising:

needle means for cutting and/or fragmenting eye tissue at a surgical site; and sleeve means, coaxially disposed about the needle means and defining a generally annular chamber between said needle means and sleeve means, for introducing a fluid into the surgical site, said needle means including shoulder means, having a conical surface of revolution and a plurality of recesses formed within the conical surface, for inhibiting bubble and microbubble formation in fluid passing between the shoulder means and the sleeve means.

2. The phacoemulsification needle apparatus according to claim 1 wherein the recesses are wedge shaped.

3. The phacoemulsification needle apparatus according to claim 2 wherein each wedge shaped recess includes a first surface disposed generally parallel to a longitudinal axis of the needle means and a second surface disposed at an obtuse angle with respect to said first surface.

4. The phacoemulsification needle apparatus according to claim 1 wherein the recesses are equidistantly spaced about the shoulder means.

5. A phacoemulsification needle apparatus comprising:

needle means, including a proximal end and a distal end, for cutting and/or fragmenting eye tissue at a surgical site, said needle means including means, disposed on said proximal end, for enabling removable engagement of the needle means with a suitable phacoemulsification horn;

sleeve means, coaxially disposed about the needle means and defining a generally annular chamber between said needle means and sleeve means, for introducing a fluid into the surgical site; and means, defined by structure on said needle means, for inhibiting formation of bubbles and microbubbles resulting from cavitation, in the annular chamber, of the fluid introduced into the surgical site, said structure including a shoulder disposed at the needle proximal end, said shoulder having at least three wedge shaped recesses formed therein, each wedge shaped recess being equidistantly spaced around said shoulder.

6. The phacoemulsification needle apparatus according to claim 5 wherein the at least three wedge shaped recesses comprises three wedge shaped recesses.

7. The phacoemulsification needle apparatus according to claim 6 wherein the means for enabling removable engagement comprises threading on said proximal end.

8. The phacoemulsification needle apparatus according to claim 7 wherein each wedge shaped recess includes first surface means for facilitating the removable engagement to the horn by manual rotation of the needle means, said first surface means being disposed generally parallel to a longitudinal axis of said needle means.

9. The phacoemulsification needle apparatus according to claim 5 wherein the shoulder includes a conical surface of revolution, and each wedge shaped recess includes a first surface being generally parallel to a longitudinal axis of the needle means and a second surface forming an obtuse angle with the first surface.

10. A phacoemulsification handpiece apparatus for ophthalmic surgical procedures, the apparatus comprising:

needle means, including a proximal end and a distal end, for cutting and/or fragmenting eye tissue at a surgical site;

sleeve means, coaxially disposed about the needle means and defining a generally annular chamber between said needle means and sleeve means, for introducing a fluid into the surgical site; and means for inhibiting formation of bubbles and microbubbles resulting from cavitation of the fluid during introduction into the surgical site, said means for inhibiting including a shoulder on the proximal end of the needle means, said shoulder having at least three wedge shaped recesses therein, said wedge shaped recesses being equidistantly spaced about said shoulder.

11. The phacoemulsification handpiece apparatus according to claim 10 wherein the at least three wedge shaped recesses comprises three wedge shaped recesses.

12. The phacoemulsification needle apparatus according to claim 10 wherein the shoulder includes a conical surface of revolution, and each wedge shaped recess includes a first surface being generally parallel to a longitudinal axis of the needle means and a second surface forming an obtuse angle with the first surface.

13. A phacoemulsification handpiece apparatus for ophthalmic surgical procedures, the apparatus comprising:

needle means for cutting and/or fragmenting eye tissue at a surgical site, said needle means including a shoulder on a proximal end thereof, said shoulder having a conical surface of revolution;

sleeve means, coaxially disposed about the needle means and defining a generally annular chamber between said needle means and sleeve means, for introducing an irrigation fluid into the surgical site; and means for inhibiting formation of bubbles and microbubbles resulting from cavitation of the irrigation fluid in the annular chamber, during introduction of the irrigation fluid into the surgical site, said means for inhibiting formation of bubbles and microbubbles including three wedge shaped recesses equidistantly spaced around said shoulder, each wedge shaped recess including a first surface disposed generally parallel to a longitudinal axis of said needle means and a second surface disposed at an obtuse angle with respect to said first surface; and means, disposed at the proximal end of the needle means, for enabling removable engagement of the needle means with a suitable phacoemulsification horn.

* * * * *